United States Patent [19]

Tennigkeit et al.

[11] Patent Number: 4,776,856
[45] Date of Patent: Oct. 11, 1988

[54] PROCESS AND MEANS FOR OXIDIZED DYEING OF HAIR USING A MANGANESE DIOXIDE CATALYST

[75] Inventors: Jürgen Tennigkeit, Seeheim; Herbert Lorenz, Gross-Bieberau, both of Fed. Rep. of Germany

[73] Assignee: Goldwell GmbH Chemische Fabrik H. E. Dotter, Darmstadt-Eberstadt, Fed. Rep. of Germany

[21] Appl. No.: 51,687

[22] PCT Filed: Aug. 7, 1986

[86] PCT No.: PCT/EP86/00466
§ 371 Date: Apr. 22, 1987
§ 102(e) Date: Apr. 22, 1987

[87] PCT Pub. No.: WO87/01033
PCT Pub. Date: Feb. 26, 1987

[30] Foreign Application Priority Data

Aug. 24, 1985 [DE] Fed. Rep. of Germany ....... 3530270

[51] Int. Cl.$^4$ ............................ A61K 7/13; A61K 7/09
[52] U.S. Cl. ............................................. 8/406; 8/405; 8/628; 132/203; 132/208; 252/186.21; 424/71
[58] Field of Search ........................... 8/405, 406, 628; 424/71, 72; 132/7; 252/186.21

[56] References Cited

U.S. PATENT DOCUMENTS

| 3,399,682 | 9/1968 | Isaji | 132/7 |
| 3,915,952 | 10/1975 | Sailer et al. | 8/437 |
| 3,973,574 | 8/1976 | Minagawa | 132/7 |
| 4,004,877 | 1/1977 | Saphir | 8/416 |
| 4,630,621 | 12/1986 | Pontani | 132/7 |

FOREIGN PATENT DOCUMENTS 1439307 4/1976 France .
2222001 11/1973 Fed. Rep. of Germany .

OTHER PUBLICATIONS

Chem. Abs. 89:168955b, Yoshida, Nov. 1978.
Chem. Abs. 90:109799b, Sunstar, Apr. 1979.

Primary Examiner—Paul Lieberman
Assistant Examiner—Linda D. Skaling

[57] ABSTRACT

In a process for the oxidative dyeing of human or animal hair, a hair dyeing agent is prepared immediately before use from at least one oxidation dye and an oxidizing agent, applied to the hair to be dyed, and made to act for a given period of time, whereupon the hair dyeing agent is washed out. The hair dyeing agent that is to be used is prepared from an oxidation dye and the oxidizing agent with the concomitant use of manganese dioxide in powder form, while the finished hair dyeing agent is adjusted to a weakly acid pH in the range from 5.9 to 6.9.

11 Claims, No Drawings

PROCESS AND MEANS FOR OXIDIZED DYEING OF HAIR USING A MANGANESE DIOXIDE CATALYST

The invention relates to a process for the oxidized dyeing of human or animal hair, in which a hair dyeing agent is prepared immediately before use from at least one oxidation dye and one oxidizing agent, applied to the hair that is to be dyed, and made to act for a given period of time, whereupon the hair dyeing agent is washed out, as well as a hair dyeing agent for performing the process.

For the lasting dyeing of human hair, alkaline oxidation dyes in paste form are used, which are mixed immediately before use with an acid oxidizing agent, e.g., hydrogen peroxide, to form the ready-to-use hair dyeing preparation that is to be applied to the hair being dyed. The color is produced by the reaction of certain developer substances with certain coupling substances in the presence of a suitable oxidizing agent. The ready-to-use preparation in this case is definitely in the alkaline range, so that the surfaces of the hairs to be dyed are opened up advantageously for the penetration of the oxidation dyes. On the other hand, alkaline preparations also are stressful to the hair, so that, especially when they are used repeatedly, e.g., for repeated redyeing, they can harm the hair. Such redyeing, however, is necessary, especially in the case of light-colored hair, in order, for example, to match the undyed regrowth to the color of the previously dyed hair lengths, or to refresh the color of the previously dyed hair lengths if the original color has faded in the course of time due to other influences, such as sunshine, frequent washing and the like.

Attempts to prevent the harmful effects, especially at the hair ends, of alkaline hair dyeing agents by acidifying the preparations ready-made from the oxidation dye and the oxidizing agent have led to insufficient coloring of the hair and therefore have not been further pursued.

The invention is addressed to the problem of devising a process for the oxidizing dyeing of hair as well as the hair dyeing agent necessary for the purpose, which, even when frequently used, will not result in the hair damage described above.

Setting out from a process of the kind described above, this object is achieved according to the invention by the use of a hair dyeing agent prepared in powder form from an oxidation dye and oxidizing agents with the use of manganese dioxide, and adjusted to a weakly acid pH in the range from 5.9 to 6.9. It has been found that, when such a hair dyeing agent with a weakly acid adjustment is used in the company of manganese dioxide, outstandingly persistent dyeing of human hair in bright shades is possible, unless darker hair is to be redyed to a lighter shade. The successful dyeing action, in comparison to earlier experiments with acid hair dyeing agents, is attributed to the catalytic action of the manganese dioxide contained in the hair dyeing agent. Furthermore it was found that the hair damage which was to be attributed to the alkalinity of the previously used hair dyeing agents is completely avoided.

From the above information it appears that, for the lightening or brightening of darker hair, recourse must be had to the known alkaline hair dyeing agents. Since damage to the hair is produced by such alkaline hair dyeing agents as a rule only after repeated redyeing, such damage can be prevented if, in the redyeing of hair dyed to a lighter color, which in the natural state is darker, the procedure is first to employ a known hair dyeing agent of alkaline adjustment on the darker regrowth close to the scalp, but in the adjoining, previously dyed hair lengths to apply the weakly acid hair dyeing agent, and to wash both the alkaline and the weakly acid hair dyeing agents out of the treated hair after a sufficient time of action.

Especially problematical in regard to hair damage is a combined permanent wave and hair dyeing treatment. In a process for the waving and oxidation dyeing of hair in which first a permanent-wave preparation is made to act for a given period of time on the hair washed and wound on curlers, and then washed out, and then the still-wound hair is pre-fixed with a liquid oxidizing fixing agent, and lastly the hair is freed from the curlers and refixed in an additional treatment step with an oxidizing fixing agent, the danger of hair damage is substantially reduced by using the weakly acid hair dyeing agent for the second fixing, letting it act on the hair for the length of time necessary for the sufficient coloring of the hair, and then washing it out. The hair dyeing agent therefore replaces the fixing agent used ordinarily in permanent waving for the second fixing, i.e., it serves a double purpose, while the damage to be feared in the use of alkaline hair dyeing means is avoided.

The hair dyeing agent used in the process according to the invention, which is prepared before application from an oxidizing dye and an oxidizing agent—liquid as a rule—can be produced by adding the manganese dioxide powder to the oxidizing dye before the addition of the oxidizing agent.

Alternatively, the manganese dioxide powder can be added simultaneously with or immediately after the oxidizing dye is mixed with the oxidizing agent in the preparation of the hair dyeing agent. The addition of manganese dioxide powder to the hair dyeing agent in such an amount that it is contained in the hair dyeing agent in a percentage between 0.02 and 5 weight-percent, preferably between 0.12 and 0.18 weight-percent, has proven to be of optimum effectiveness.

The preparation produced by mixing an oxidizing dye with an oxidizing agent immediately before use in the performance of the process according to the invention is therefore characterized by being adjusted to a pH between 5.9 and 6.9, and additionally contains finely divided manganese dioxide in powder form.

The amount of the manganese dioxide is preferably such that it is contained in the hair dyeing agent in percentages between 0.02 and 5 weight-percent, preferably between 0.12 and 0.18 weight-percent.

EXAMPLE 1a

Oxidation Dyeing 20 ml of dye paste of the formula given below for the color, hazelnut blonde, with the addition of 0.12% of manganese(IV) oxide in finely divided form, was mixed with 40 ml of a developer solution containing 2% of hydrogen peroxide, resulting in a hair dyeing agent with a pH of 6.7. The agent was applied to a medium-weight hair with a medium ash-blonde basic shade, and allowed to act for 20 minutes.

The result was a recoloring of the hair to an intense hazelnut blonde shade.

Experiments showed that the time of action of the hair dyeing agent can be reduced to 5 minutes with a correspondingly lower resultant color intensity.

| Formula of the "Hazelnut Blonde" Dye Paste: | |
|---|---|
| cetylstearyl alcohol | 10.0 g |
| coconut fatty acid monoethanolamide | 2.0 g |
| stearic acid monoethanolamide | 2.0 g |
| stearic acid diethanolamide | 1.0 g |
| p-toluylenediamine sulfate | 0.25 g |
| m-aminophenol | 0.01 g |
| resorcinol | 0.01 g |
| p-aminophenol | 0.08 g |
| p-amino-o-cresol | 0.06 g |
| picraminic acid | 0.05 g |
| monoethanolamine | 0.2 g |
| ammonium chloride | 0.2 g |
| sodium lauryl sulfate | 0.3 g |
| manganese(IV) oxide | 0.12 g |
| sodium sulfite | 0.2 g |
| ethylenediaminetetraacetic acid | 0.2 g |
| perfume | 0.2 g |
| softened water to make | 100.00 g |

EXAMPLE 1b

Oxidizing Dye 20 ml of the dye paste of the formula given below for the color "Copper Blonde" with the addition of 0.12% of manganese(IV) oxide in finely divided form was mixed with 40 ml of a developer solution containing 2% of hydrogen peroxide, resulting in a hair dyeing agent with a pH of 6.7.

The dyeing agent was applied to a medium-weight hair with a medium ash-blonde basic shade and allowed to act for 20 minutes.

As a result the hair was dyed to a discreet copper shade.

Experiments showed that the time of action of the hair dyeing agent can be shortened to only 5 minutes with a correspondingly reduced resultant color intensity.

| Formula for the "Copper Blonde" Dye Paste | |
|---|---|
| cetylstearyl alcohol | 10.0 g |
| coconut fatty acid monoethanolamide | 2.0 g |
| stearic acid monoethanolamide | 2.0 g |
| stearic acid diethanolamide | 1.0 g |
| p-toluylenediamine sulfate | 0.20 g |
| p-aminophenol | 0.70 g |
| p-amino-o-cresol | 0.70 g |
| monoethanolamine | 0.2 g |
| ammonium chloride | 0.2 g |
| sodium laurylsulfate | 0.3 g |
| manganese(IV) oxide | 0.12 g |
| sodium sulfite | 0.12 g |
| ethylenediaminetetraacetic acid | 0.2 g |
| perfume | 0.2 g |
| softened water to make | 100.00 g |

EXAMPLE 2

Oxidation Dyeing for a Gentle, Acid Equalization of the Hair Ends After a Normal, Alkaline Initial Dyeing 20 ml of dye paste of the formula given in Example 1a for the hair color "Hazelnut Blonde" with an addition of 0.12% of manganese(IV) oxide in finely divided form, was mixed with 40 ml of a developer solution containing 2% of hydrogen peroxide, resulting in a hair dye with a pH of 6.7.

The dye was applied to a medium-heavy hair which had been dyed hazelnut blonde and whose lengths and ends had faded and had a light ash blonde tone, and allowed to act for 10 minutes.

As a result, a hazelnut blonde shade equalized with the initial dye of the bleached lengths and ends was obtained. The time of action of the preparation can be shortened to 5 minutes at lesser equalizing color intensities.

EXAMPLE 3a

Oxidation Dyeing Combined with Permanent Waving

A permanent wave was performed on medium-heavy hair which had a basic color of dark golden blonde, and in which the hair lengths and ends had faded.

The permanent wave was performed on the curler according to instructions up to and including the first fixing.

For the final fixing and simultaneous dyeing, the curler was removed and 20 ml of dye paste of the formula given below for the color, "cyclamen," with an addition of 0.12% of manganese(IV) oxide in finely divided form, was mixed with 40 ml of a permanent wave fixer with a hydrogen peroxide content of 2%.

The resultant hair dyeing agent with a pH of 6.7 was then applied to the hair with an applicator bottle and a sponge and allowed to work for 10 minutes. The result was a redyeing of the hair to a reddish violet (cyclamen) shade in addition to the permanent wave. The working time can be varied between 5 and 20 minutes according to the desired color intensity.

| Formula for "Cyclamen" Hair Dye Paste | |
|---|---|
| cetylstearyl alcohol | 10.0 g |
| coconut fatty acid monoethanolamide | 2.0 g |
| stearic acid monoethanolamide | 2.0 g |
| stearic acid diethanolamide | 1.0 g |
| p-toluylenediamine sulfate | 0.5 g |
| p-amino-o-cresol | 0.4 g |
| p-aminophenol | 0.1 g |
| monoethanolamine | 0.2 g |
| ammonium chloride | 0.2 g |
| sodium lauryl sulfate | 0.3 g |
| manganese(IV) oxide | 0.12 g |
| sodium sulfite | 0.25 g |
| ethylenediaminetetraacetic acid | 0.2 g |
| perfume | 0.2 g |
| softened water to make | 100.0 g |

EXAMPLE 3b

Oxidation Dyeing Combined with Permanent Wave

A permanent wave was performed on medium-heavy hair which had a basic color of golden blond and in which the hair lengths and ends had faded.

The permanent wave was performed on the curler according to instructions up to and including the first fixing.

For the second fixing and simultaneous dyeing, the curlers were removed and 20 ml of dye paste of the formula given below for the color "Mahogany" with the addition of 0.12% manganese(IV) oxide in finely divided form was mixed with 40 ml of a permanent wave fixer with a hydrogen peroxide content of 2%.

The resultant hair dyeing agent with a pH of 6.7 was then applied to the hair with an applicator bottle and a sponge swab and allowed to work for 10 minutes. As the result, the hair was redyed to a strong red shade in addition to the permanent wave. The working time can be varied between 5 and 20 minutes according to the desired color intensity.

| Formula for "Mahogany" Dye Paste | |
|---|---|
| cetylstearyl alcohol | 10.0 g |
| coconut fatty acid monoethanolamide | 2.0 g |
| stearic acid monoethanolamide | 2.0 g |
| stearic acid diethanolamide | 1.0 g |
| p-toluylenediamine sulfate | 0.4 g |
| p-aminophenol | 0.4 g |
| p-amino-o-cresol | 0.4 g |
| o-nitro-p-phenylenediamine | 0.4 g |
| monoethanolamine | 0.2 g |
| ammonium chloride | 0.2 g |
| sodium lauryl sulfate | 0.3 g |
| manganese(IV) oxide | 0.12 g |
| sodium sulfite | 0.25 g |
| ethylenediaminetetraacetic acid | 0.2 g |
| perfume | 0.2 g |
| softened water to make | 100.0 g |

We claim:

1. A method of dyeing human or animal hair, comprising the steps of: preparing a dyeing agent having a pH between 5.9 and 6.9, from a mixture of approximately one-third by weight of an aqueous oxidation dye paste containing an effective amount of an oxidation dye, and approximately two-thirds by weight of a developer solution containing approximately two percent of hydrogen peroxide, and 0.02 to 5 percent by weight of powdered manganese dioxide as a catalyst; immediately thereafter applying said dyeing agent to the hair and letting the same act on the hair for a period of time sufficient to dye the hair; and washing the dyeing agent out of the hair.

2. A method of re-dyeing human or animal hair which in natural state is dark and has previously been dyed to a lighter state, comprising the steps of: applying a first conventional alkalinely adjusted hair dyeing agent to recent growth of darker hair close to the scalp, preparing a second dyeing agent having a pH between 5.9 and 6.9, from a mixture of approximately one-third by weight of an aqueous oxidation dye paste containing an effective amount of an oxidation dye, and approximately two-thirds by weight of a developer solution containing approximately two percent of hydrogen peroxide, and 0.02 to 5 percent by weight of powdered manganese dioxide as a catalyst; immediately thereafter applying said dyeing second agent to the lighter state hair adjacent to the recent growth of hair and letting the same act on the lighter state hair for a period of time sufficient to dye the hair; and washing both dyeing agents out of the hair.

3. A method of waving and dyeing human or animal hair, comprising the steps of: applying a conventional permanent-wave preparation to the hair, which has previously been washed and wound on curlers, for a given period of time, washing out the hair, fixing the hair, still wound on the curlers, with a conventional liquid oxidizing fixing agent; removing the curlers, and re-fixing the hair with a dyeing agent having a pH between 5.9 and 6.9, from a mixture of approximately one-third by weight of an aqueous oxidation dye paste containing an effective amount of an oxidation dye, and approximately two-thirds by weight of a developer solution containing approximately two percent of hydrogen peroxide, and 0.02 to 5 percent by weight of powdered manganese dioxide as a catalyst; letting the dyeing agent act on the hair for a period of time sufficient to dye the hair, and washing the dyeing agent out of the hair.

4. A method according to any one of claims 1 to 3, wherein the percentage of the powdered manganese dioxide is 0.12 to 0.18.

5. A method of preparing a dyeing agent for human or animal hair, comprising the steps of: mixing approximately one-third by weight of an aqueous oxidation dye paste containing an effective amount of an oxidation dye, and approximately two-thirds by weight of a developer solution containing approximately two percent of hydrogen peroxide, and 0.02 to 5 percent by weight of a powdered manganese dioxide as a catalyst so as to result in a dyeing agent having a pH between 5.9 and 6.9.

6. A method according to claim 5, wherein the percentage by weight of the powdered manganese dioxide is 0.12 to 0.18.

7. A method according to claim 5, wherein the manganese dioxide is mixed with the oxidation dye, prior to the addition of the oxidizer.

8. A method according to claim 5, wherein the manganese dioxide is mixed with the oxidation dye, after the addition of the oxidizer.

9. A method according to claim 5, wherein the manganese dioxide is mixed with the oxidation dye, simultaneously with the addition of the oxidizer.

10. An agent for dyeing human or animal hair, comprising: a mixture of approximately one-third by weight of an aqueous oxidation dye paste containing an effective amount of an oxidation dye, and approximately two-thirds by weight of a developer solution containing approximately two percent of hydrogen peroxide, and 0.02 to 5 percent by weight of powdered manganese dioxide as a catalyst; said agent having a pH between 5.9 and 6.9.

11. An agent according to claim 10, wherein the percentage by weight of the powdered manganese dioxide is 0.12 to 0.18.

* * * * *